(12) United States Patent
Schulte et al.

(10) Patent No.: US 9,341,515 B2
(45) Date of Patent: May 17, 2016

(54) OPTICAL ABSORBANCE MEASUREMENT APPARATUS, METHOD, AND APPLICATIONS

(75) Inventors: Alfons Schulte, Orlando, FL (US); Silki Arora, Orlando, FL (US)

(73) Assignee: University of Central Florida Research Foundation, Inc., Orlando, FL (US)

(*) Notice: Subject to any disclaimer, the term of this patent is extended or adjusted under 35 U.S.C. 154(b) by 728 days.

(21) Appl. No.: 13/370,969

(22) Filed: Feb. 10, 2012

(65) Prior Publication Data

US 2012/0206727 A1  Aug. 16, 2012

Related U.S. Application Data

(60) Provisional application No. 61/441,684, filed on Feb. 11, 2011.

(51) Int. Cl.
*G01J 3/42* (2006.01)
*G02B 21/00* (2006.01)
(Continued)

(52) U.S. Cl.
CPC ............... *G01J 3/42* (2013.01); *G01J 3/0208* (2013.01); *G01J 3/0229* (2013.01); *G01J 3/0289* (2013.01); *G01J 3/427* (2013.01); *G01N 21/03* (2013.01); *G01N 21/31* (2013.01); *G01N 21/314* (2013.01); *G02B 21/0028* (2013.01); *G02B 21/0032* (2013.01); *G02B 21/26* (2013.01); *G02B 21/367* (2013.01); *G01N 21/3151* (2013.01); *G01N 2021/0346* (2013.01); *G01N 2021/058* (2013.01); *G01N 2021/651* (2013.01); *G01N 2021/656* (2013.01); *G01N 2201/0627* (2013.01); *G01N 2201/0846* (2013.01)

(58) Field of Classification Search
CPC .............................. G01N 2201/0846
See application file for complete search history.

(56) References Cited

U.S. PATENT DOCUMENTS 4,989,942 A * 2/1991 Koenigsberg et al. ........ 356/436
5,048,959 A * 9/1991 Morris et al. .................. 356/301
(Continued)

FOREIGN PATENT DOCUMENTS

WO    2004008217 A1    1/2004

OTHER PUBLICATIONS

Itzkan et al., Confocal light absorption and scattering spectroscopic microscopy monitors organelles in live cells with no exogenous labels, PNAS, Oct. 30, 2007, vol. 104, No. 44, 17255-17260.
(Continued)

*Primary Examiner* — Gordon J Stock, Jr.
(74) *Attorney, Agent, or Firm* — William Greener; Bond, Schoeneck & King, PLLC

(57) ABSTRACT

Apparatus and method to measure optical absorption spectra with spatial resolution on the micron scale. An exemplary setup combines a continuous white light excitation beam in transmission geometry with a confocal microscope. Spatial resolution better than 1.4 μm in the lateral and 3.6 μm in the axial, directions was obtained. The detection and measurement of the absorption spectrum of hemoglobin in a single red blood cell under physiological conditions on the timescale of seconds was realized. The apparatus and method enables the investigation of spatial variations in the optical density of small samples on the micron scale and the study of biological assemblies at the single cell level, leading to applications in optical diagnostics, microfluidics, and other areas.

31 Claims, 7 Drawing Sheets

(51) Int. Cl.
*G01J 3/02* (2006.01)
*G01J 3/427* (2006.01)
*G01N 21/03* (2006.01)
*G01N 21/31* (2006.01)
*G02B 21/26* (2006.01)
*G02B 21/36* (2006.01)
*G01N 21/05* (2006.01)
*G01N 21/65* (2006.01)

(56) References Cited

U.S. PATENT DOCUMENTS

| | | | | |
|---|---|---|---|---|
| 5,302,272 | A * | 4/1994 | Klein | 204/603 |
| 5,528,368 | A * | 6/1996 | Lewis et al. | 356/456 |
| 5,713,364 | A * | 2/1998 | DeBaryshe et al. | 600/476 |
| 6,128,077 | A | 10/2000 | Jovin et al. | |
| 6,370,422 | B1 * | 4/2002 | Richards-Kortum et al. | 600/478 |
| 6,628,382 | B2 * | 9/2003 | Robertson | 356/246 |
| 6,747,795 | B2 * | 6/2004 | Lin et al. | 359/385 |
| 6,809,826 | B2 * | 10/2004 | Robertson | 356/440 |
| 6,865,408 | B1 * | 3/2005 | Abbink et al. | 600/310 |
| 7,268,938 | B2 | 9/2007 | Kawano et al. | |
| 7,969,575 | B2 * | 6/2011 | Zuo | 356/432 |
| 8,049,884 | B2 * | 11/2011 | Tsukuda | 356/326 |
| 8,189,199 | B2 * | 5/2012 | Robertson et al. | 356/440 |
| 8,223,338 | B2 * | 7/2012 | Robertson et al. | 356/440 |
| 2001/0007496 | A1 * | 7/2001 | Modlin et al. | 356/73 |
| 2003/0053050 | A1 * | 3/2003 | Potyrailo et al. | 356/326 |
| 2003/0054337 | A1 * | 3/2003 | Birkett | 435/5 |
| 2003/0098419 | A1 * | 5/2003 | Ji et al. | 250/373 |
| 2004/0029266 | A1 * | 2/2004 | Barbera-Guillem | 435/297.5 |
| 2007/0060809 | A1 * | 3/2007 | Higgins | 600/328 |
| 2007/0081159 | A1 * | 4/2007 | Giffin et al. | 356/319 |
| 2011/0063433 | A1 * | 3/2011 | Thonhauser | 348/135 |
| 2012/0242992 | A1 * | 9/2012 | Schulte et al. | 356/432 |

OTHER PUBLICATIONS

Grlj, Natasa (Contact), SPIRIT—Confocal spectroscopy, Microanalytical Center—MIC Department for Low and Medium Energy Physics—F2, Jozef Stefan Institute Reactor Center, http://www.rcp.ijs.si/mic/SPIRITconfocal.php, printed out on Feb. 9, 2011.

Bigelow, et al.; Confocal Fluorescence spectroscopy and anisotropy imaging system, Opticis Letters, vol. 28, Issue 9, pp. 695-697 (2003), 2010, Optical Society of America, http://www.opticsinfobase.org/abstract.cfm?uri=ol-28-9-695.

Jean et al., Fibered confocal spectroscopy and multicolor imaging system for in vivo fluorescence analysis, Optics Express, vol. 15, Issue 7 pp. 4008-4017 92007), 2010, Optical Society of America, http://www.opticsinfobase.org/oe/abstract.cfm?uri=oe-15-7-4008.

* cited by examiner

2a

2b

3a

3b

OPTICAL ABSORBANCE MEASUREMENT APPARATUS, METHOD, AND APPLICATIONS

GOVERNMENT SPONSORSHIP

N/A.

TECHNICAL FIELD

Embodiments of the present invention relate generally to optical systems, associated methods, and applications thereof enabling the measurement of, and use of, spatially resolved optical absorbance and variations in optical density of a sample). More particularly, embodiments pertain to such optical systems, associated methods, and applications directed to absorption spectroscopy, and even more particularly to confocal absorption spectroscopy employing broadband excitation.

BACKGROUND

The ability to investigate structure and dynamics on a micron scale with non-destructive optical probes is key to studies at the single cell level and applications in microfluidics. Confocal microscopy is a technique that provides enhanced resolution due to elimination of out of focus rays by a spatial filter (pinhole) or by multi-photon excitation. For confocal detection, a pinhole is located in the conjugate plane of the focal plane (defined by the collection optics), which enables optical sectioning along the axial direction.

Fluorescence probes employing confocal or other geometries are well established; however they generally require labeling and are limited by photobleaching and quenching. Micro-spectroscopy based on absorption measurements provides a convenient label free way for characterizing an unknown material. Fourier-transform infrared (FTIR) spectroscopic imaging relying on vibrational signatures has numerous applications. Though light scattering has been used recently as a source of contrast in the visible, standard confocal microscopy so far lacks the capability for direct optical absorption profile measurements.

A difficulty for measurements with axial resolution is presented by the 'missing cone' problem (see, e.g., M. B. Cannell, A. McMorland and C. Soeller, "Image enhancement by deconvolution", *Handbook of biological confocal microscopy*, J. B. Pawley Ed. (Springer, New York, N.Y., 2006), $3^{rd}$ ed., Chap. 25, pp. 488-500). The optical transfer function is angularly band limited, so that the longitudinal resolution in the axial direction is degraded. To provide spatial discrimination in the axial direction, a confocal laser absorption microscope has been reported. An excitation laser pulse irradiates the sample so that ground-state molecules transit to the excited state, thus creating a spatial distribution of molecules, similarly to what is used in confocal fluorescence. The absorption to higher energy levels is then probed by a monitoring laser beam introduced coaxially. An excited state absorption profile is obtained by scanning the sample. In general the absorption of the laser beam due to electronic transitions from the ground state is assumed to be negligible, although the attenuation of the propagating light could provide a mechanism for contrast in the axial direction.

More simply, the lack of adequate spatial resolution limited the ability to practically measure absorbance in a single cell. Small samples let too much light through the system.

The inventors have recognized the advantages and benefits of a practical and robust solution directed especially to enabling micron-scale axial and lateral resolution absorption spectroscopy to study cells in their native environment and other biological assemblies. For example, the ability to acquire micron-scale absorption measurements of single live erythrocytes in nanoliter volume solutions in micro-capillaries or microchannels, and to determine variations in composition of inhomogeneous samples (e. g. thin films of a few microns), to detect malaria, to monitor blood bank quality by measuring absorption spectrum changes in aging blood cells, to monitor body fluids for pregnancy and AIDS testing, for intrinsic imaging, and other applications and capabilities would be advantageous, especially in microfluidics and nanomaterials characterization.

SUMMARY

By exploiting the spatial variation of the intensity due to the Beer-Lambert law, we demonstrate a novel approach to obtain ground state absorption spectra with a spatial resolution of better than 1.4 µm in the lateral and 3.6 µm in the axial directions. An embodied method employs a confocal detection system to probe and spectrally resolve the attenuation of a white light beam in the axial direction. The method enables the measurement of absorption spectra of biological assemblies at the single cell level and of small samples with a thickness of few microns. Confocal absorption microscopy (CAM) is nondestructive and is capable of collecting both spatial and physical information based on light absorption by microscopic structures.

An embodiment of the invention is a transmission-geometry, optical absorbance spectroscopy apparatus. The apparatus may comprise a stand-alone sample illumination apparatus that includes a broadband sample illumination source; a broadband sample illumination propagation medium; a sample holder; and a sample field-of-view controller coupled to the broadband sample illumination source and the sample holder, characterized by a sample field of view having a maximum dimension less than 50 micrometers (µm), more particularly, equal to or less than about 35 µm, and most particularly, equal to or less than about 25 µm. In various, non-limiting aspects, the apparatus may further include as features, components, or limitations, the following:
wherein the broadband sample illumination source is a broadband white light source;
wherein the broadband sample illumination source comprises at least two illumination sources having different illumination spectra;
  wherein the at least two illumination sources include at least two light emitting diodes (LEDs);
wherein the sample illumination propagation medium is an optical waveguide;
wherein the sample holder is adapted to hold at least one of a microcapillary and a microfluidic device having a microchannel;
  wherein the sample holder further comprises an x-y-z translation stage on which the sample holder is mounted;
wherein the sample field-of-view controller has an aperture having a clear aperture diameter between about 5 to 25 µm;
  further comprising an optical waveguide having a proximal end coupled to the sample illumination source and a distal end, wherein the sample field-of-view aperture is disposed at the distal end of the optical waveguide, which is coupled to the sample holder;
further comprising an optical microscope adapted to collect the sample illumination transmitted by the sample; and a detector adapted to receive an output of the optical microscope;
  wherein the detector further comprises a spectrometer;

wherein the sample-field of view controller has an aperture having a clear aperture diameter between about 5 to 35 µm;
  further comprising an optical waveguide having a proximal end coupled to the sample illumination source and a distal end, wherein the sample field-of-view aperture is disposed at the distal end of the optical waveguide, which is coupled to the sample holder;
    further wherein the distal end of the optical waveguide is disposed in an alignment fixture that is seated in a given location of the sample holder;
      further comprising an x-y-z translation stage on which the sample holder is mounted;
wherein the broadband sample illumination source is a broadband white light source;
wherein the broadband sample illumination source comprises at least two illumination sources having different illumination spectra;
  wherein the at least two illumination sources include at least two light emitting diodes (LEDs);
wherein the sample illumination propagation medium is an optical waveguide;
wherein the sample holder is adapted to hold at least one of a microcapillary and a microfluidic device having a microchannel;
  wherein the sample holder further comprises an x-y-z translation stage on which the sample holder is mounted;
wherein the optical system is a confocal system;
  comprising a free-space confocal system;
    wherein the confocal system has a confocal aperture having a diameter between about 10 to 50 microns.

An embodiment of the invention is a method for performing transmission-based optical absorption spectroscopy of a sample. The method includes the steps of illuminating a sample with a broadband illumination spectrum; and limiting a sample illumination field of view having a maximum dimension less than 50 micrometers (µm), more particularly, equal to or less than about 35 µm, and most particularly, equal to or less than about 25 µm. In various, non-limiting aspects, the method may further include as features, components, or limitations, the following:
transmitting the broadband illumination spectrum to the sample via an optical waveguide; and aperturing the illumination at an output end of the optical waveguide to limit the sample illumination field of view;
illuminating the sample with a broadband white light illumination spectrum;
confocally imaging the illumination light that is transmitted by the sample; inputting the confocally imaged light into a spectrometer; and obtaining the optical absorption spectrum of the sample;
  wherein the step of confocally imaging the illumination light that is transmitted by the sample further comprises providing a confocal aperture having a diameter between about 10 to 50 microns;
    wherein the step of obtaining the optical absorption spectrum further comprises adjusting the diameter of the confocal aperture;
further comprising scanning the sample with the illuminating light in an axial direction;
further comprising providing the sample in a micro-capillary;
further comprising providing the sample in a microchannel of a microfluidic device;
wherein the sample comprises a red blood cell;
wherein the sample further comprises a red blood cell infected with *Plasmodium falciparum*.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention, and together with the description serve to explain the principles and operation of the invention

BRIEF DESCRIPTION OF THE DRAWINGS

The present invention will be more fully understood and appreciated by reading the following Detailed Description in conjunction with the accompanying drawings, in which.

DETAILED DESCRIPTION OF NON-LIMITING, EXEMPLARY EMBODIMENTS OF THE INVENTION

Figure 1:
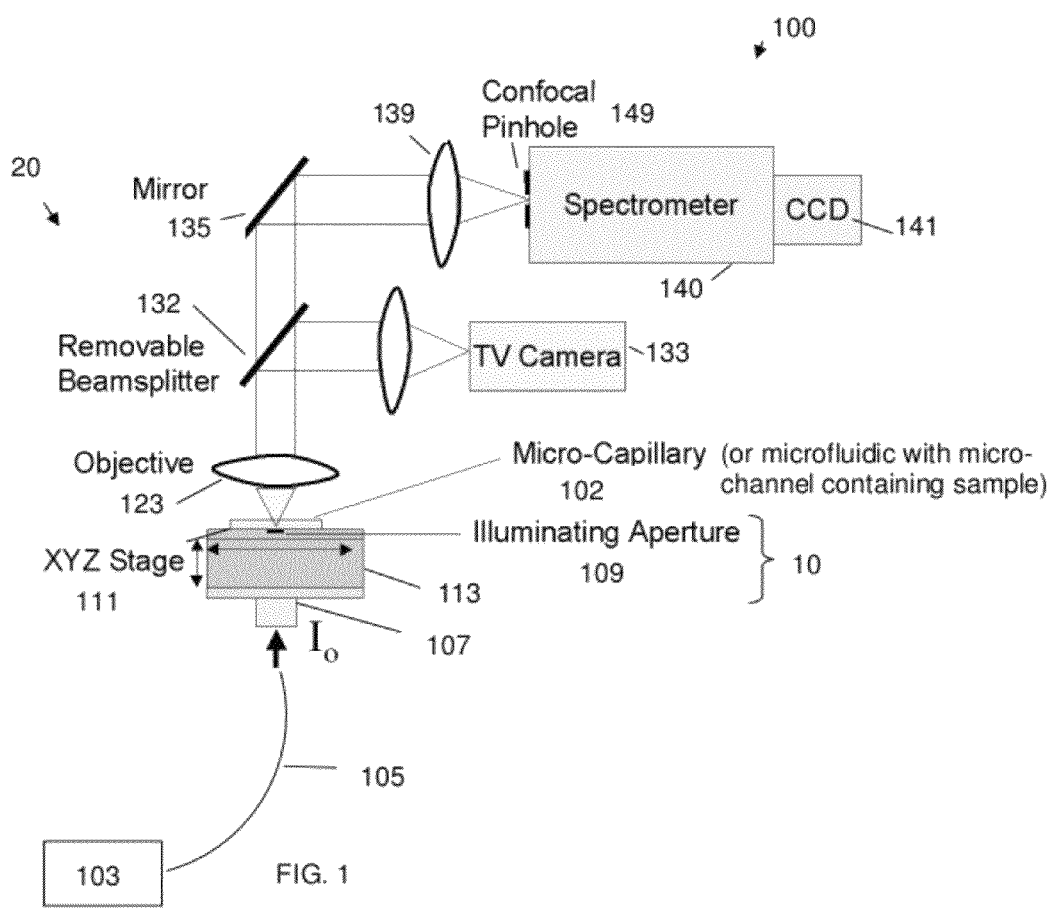
FIG. 1 shows a schematic of a confocal absorption microscopy (CAM) apparatus according to an exemplary embodiment of the invention.

A schematic diagram of an embodied optical absorbance detection apparatus referred to as a Spatially Resolved Confocal Absorption Method (CAM) apparatus 100 is shown in FIG. 1. The CAM apparatus 100 includes sample illumination component 10 composed of a broadband white light excitation source (e.g., Ocean Optics LS1 tungsten halogen lamp) 103 that is utilized to illuminate a sample (e.g., a red blood cell; however, the sample is not a component of the invention per se) disposed in a micro-capillary or microfluidic channel 102 of a microfluidic device s known in the art. In the illustrative embodiment of FIG. 1, the micro-capillary has an outer diameter of 350 μm and an inner bore of 50 μm. The broadband sample illumination is propagated via an optical waveguide in the form of an optical fiber 105 (e.g., multimode fiber having a core diameter of 400 μm, N.A.=0.22) coupled at one (proximal) end thereof to the illumination source. The distal end of the optical fiber 105 is mounted in an alignment fixture in the form of a cylinder 107 to aid in its precise alignment with the sample. A sample-field of view controller in the form of a clear aperture 109 has a clear diameter of between about 5 μm to 25 μm is disposed at the distal, sample-illuminating end of the fiber 105 in the cylinder 107. A sample-field of view controller aperture having a 5 μm to 35 μm opening limits the stray illumination light and allows illumination of only the sample inside the micro-capillary or microchannel, and contributes to improved optical resolution of the CAM apparatus.

The sample illumination component 10 of the CAM apparatus 100 further includes a sample holder 111 in the form of a light-transmitting flat surface having a V-groove at the centre for holding and aligning the micro-capillary. The fiber cylinder topped with the field of view-controller aperture is seated at the centre of the sample holder. The sample holder is mounted on a motorized XYZ stage 113.

The CAM apparatus 100 further includes an optical microscope 20. The field-of-view-limited illumination light that is transmitted (i.e., not absorbed or reflected) through the sample is collected by the optical system, which is illustrated as a free-space confocal microscope that includes a 50× (NA=0.75) dry objective lens 123 and confocal lens 139. The transmitted light then intercepts an optional, removable beam splitter 132, whereupon a portion of the light is optionally reflected to a camera 133 for optical imaging. The transmitted light intercepts a turning mirror (or beam splitter) 135 whereupon at least a portion of the light is reflected towards a spectrometer 140 including a detector 141. Confocal lens 139 focuses the light on a confocal pinhole 149, which serves as the input to the spectrometer. The confocal pinhole has a diameter between about 10 μm to 50 μm, which may be adjustable depending upon sample thickness. The spatial resolution of the CAM apparatus is determined by the confocal pinhole size.

The broadband white light source 103 may be a halogen-based lamp or other broadband illumination source known in the art. Alternatively, the broadband illumination source may be two or more LEDs (e.g., red, green, blue; not shown) whose spectral outputs can be combined by known optical means to provide a broadband spectral illumination of the sample (which may cover portions of the IR, visible, and UV spectra). The broadband illumination source may alternatively be a white light LED (not shown), which may be directly coupled to the sample holder. Infrared (IR) and ultraviolet (UV) illumination spectra may also be generated by combined or dedicated spectral sources used to illuminate the sample, as those skilled in the art would understand.

An exemplary process aspect of the embodied invention involves exploiting the spatial variation of the transmitted intensity due to the Beer-Lambert law to obtain ground state absorption spectra. In one exemplary aspect, a confocal detection system was used to probe and spectrally resolve the attenuation of a white light beam in the axial direction, enabling the measurement of absorption spectra of biological assemblies at the single cell level and of small samples with a thickness of few microns. Using the embodied apparatus and method, we achieved a spatial resolution of better than 1.4 μm in the lateral and 3.6 μm in the axial directions.

Referring again to FIG. 1, a schematic diagram of the confocal absorption microscopy (CAM) apparatus 100 method is shown, which illustrates the embodied methodology. The setup couples a broadband white light excitation source in transmission geometry with a confocal detection system (i.e., microscope+detector). A conventional tungsten-halogen lamp (102) was used to illuminate the sample through an optical fiber 105. A fiber alignment cylinder 107 topped with a field of view-limiting aperture 109 was seated at the center of a sample holder 111 having a V-groove along the longitudinal center for aligning a micro-capillary 102 having an outer diameter of 350 μm and inner bore of 50 μm. The aperture limits the stray light and only allows illumination of the sample inside the micro-capillary. The sample holder was mounted on a 3-D (XYZ) positioning stage 113, which allowed scanning the sample through the optical path.

The transmitted light was collected through a 50× (NA=0.75) dry objective lens 123, reflected by a mirror 135, and focused through a confocal lens 139 to the confocal pinhole 149 located at the entrance of a spectrometer (LabRam HR800) 140. In the optical beam coming from the microscope, a beamsplitter 132 was optionally introduced for sample observation on a TV camera (Sony CSC790) 133. Absorption spectra were acquired with a back-illuminated CCD detector 141 over a spectral range from 350 to 800 nm at a spectral resolution of 0.5 nm. The spatial resolution of the system was determined by the confocal pinhole diameter.

Experimentally, a field of view-limiting aperture with an opening of 25 μm was centered about the optical axis for maximum transmitted light intensity. The confocal pinhole at the entrance slit of the spectrometer was set to 50 μm. The aperture was then scanned through the beam along the radial direction with no sample present. The measured light intensity inside the aperture varied by less than 7% inside a 20 μm diameter. At the edge of the clear aperture the intensity increased from 10 to 90% over a distance of 1 μm. This control scenario was repeated with confocal clear apertures of 5 and 10 μm with similar results.

Another set of experiments was conducted where the size of the illuminating aperture (109, FIG. 1) was kept fixed (25 μm) while the confocal pinhole was varied from 10 to 50 μm. The light intensity plateaued inside the aperture, but the slope at the boundary became steeper with decreasing pinhole size. The lateral resolution (10 to 90% intensity points) was controlled by the confocal pinhole diameter on the detection side while the illuminating aperture (109) at the distal end of the illumination fiber limited the field of view of the sample on the excitation side.

To assess the lateral and axial resolutions in absorption measurements we examined individual red blood cells with diameter of about 6-8 μm as small absorbing objects. Red blood cells were preferred over fluorescent beads as the fluorescence emission might have distorted the absorbance signal. Erythrocytes were prepared as follows: coverslips were rinsed with 70% ethanol followed by 1× Phosphate Buffer Saline (pH 7.4). Sufficient (1 mg/ml) poly-L-Lysine HBr was applied to coat the coverslips, which were then kept at room temperature for 15 minutes. The coating solution was removed and the coverslips were rinsed with 1×PBS. The erythrocytes suspended in 1×PBS were added to the coverslips and were allowed to adhere at room temperature for 20 minutes. Excess liquid was drained from the coverslip.

The absorbance A was calculated using the relation $A = -\log(I/I_0)$. Spectra were acquired with an integration time of 5 seconds. The peak position of the Soret band in the absorption spectrum is 415 nm, and is indicative of fully oxygenated hemoglobin.

Figure 2:
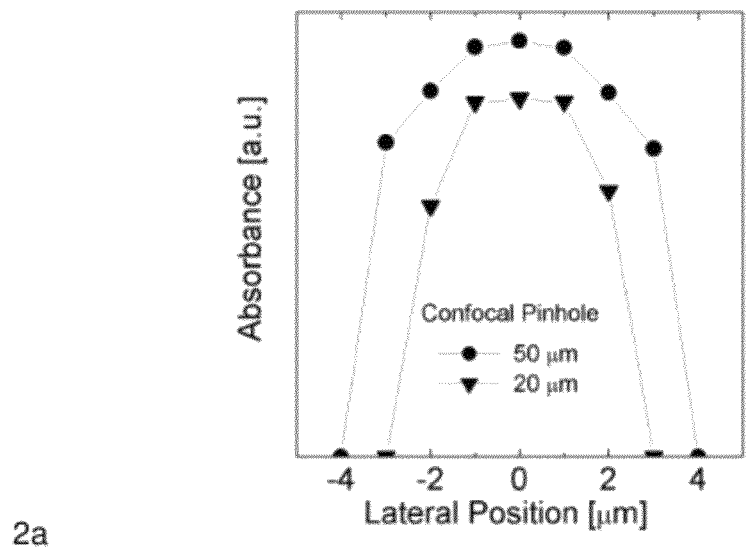
FIG. 2: Spatial variation of absorbance of a red blood cell at the peak position of the Soret band. Scans are shown in the lateral (a) and axial (b) directions, according to an illustrative aspect of the invention.
Figure 2:
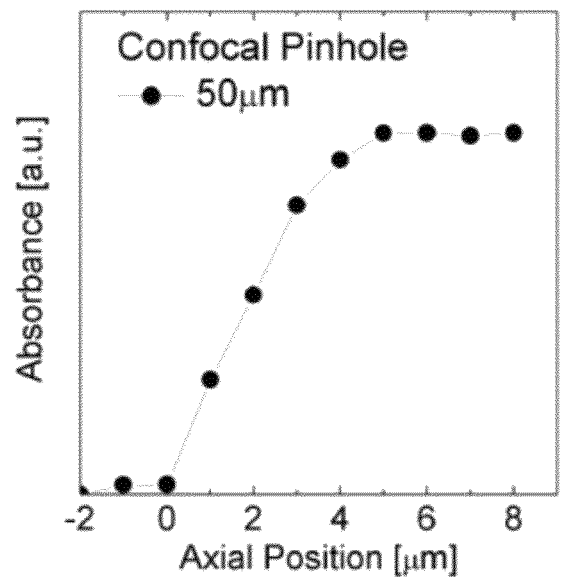

The spatial resolution was determined as follows: the slide assembly without and with cells was scanned along the lateral and axial directions and the spectral light intensities $I_o$ and I were recorded as a function of position. The variation of $I_o$ in the axial direction close to the sample was small (<10% over a distance of 100 μm) and was taken into account. From the measured intensities $I_o$ and I, a complete absorbance spectrum was obtained at each spatial location. The peak absorbance (415 nm) is plotted in FIG. 2a as a function of position for both the lateral and axial directions. The absorbance increased and then decreased as the cell was moved through the beam. The width of the plateau corresponds to the diameter of a red blood cell. The lateral resolution was determined from the 10% and 90% intensity points to 1.4 μm for a confocal pinhole size of 50 μm. In the axial direction the absorbance increased first within the erythrocyte and then remained constant, as shown in FIG. 2b. An axial resolution better than 3.6 μm was achieved.

To establish the accuracy of CAM and its ability to determine the absorption spectrum of samples with nanoliter volumes, the concentration dependence of the optical absorption of a series of solutions was measured. Experiments were performed on a solution of calcein dye (Sigma 21030; molecular Wt.: 666.5 g/mol; $\epsilon=55053$ $M^{-1}cm^{-1}$). The sample was prepared by dissolving 9.46 mg of the calcein powder in 1 ml of deionized water. The solution was stirred slowly for 10 minutes, then passed through a micro filter to remove any impurities. The final concentration of the stock solution was 14.2 mM.

Figure 3:
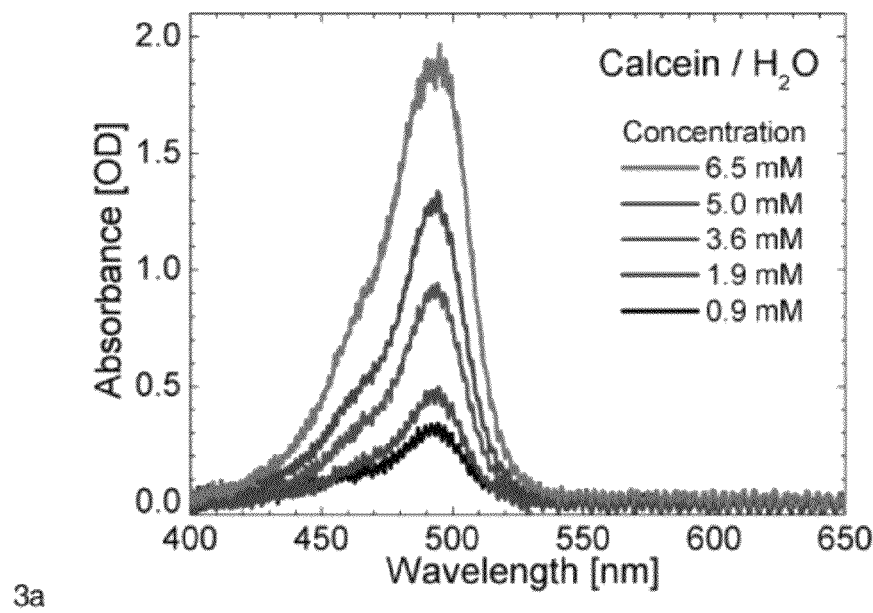
FIG. 3: a) Absorption spectrum of calcein obtained with the confocal absorption microscopy apparatus illustrated in FIG. 1; b) peak absorbance A divided by pathlength L as a function of calcein concentration, according to illustrative aspects of the invention.
Figure 3:
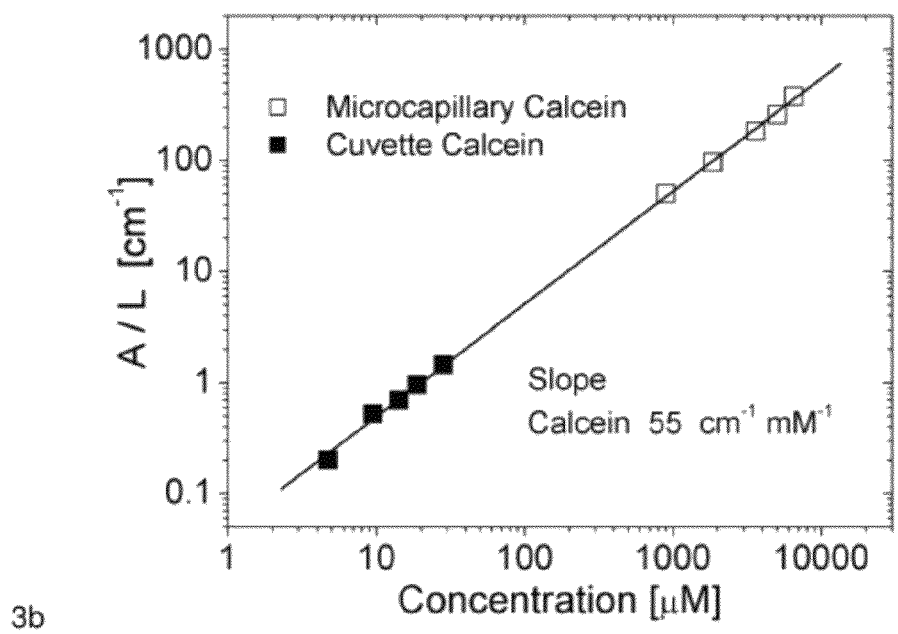

For confocal absorption spectroscopy, the sample solution was loaded into a micro-capillary of nominal inner diameter 50±5 μm. The micro-capillary was then positioned in the sample holder groove and illuminated by the broad spectrum white light source using the optical fiber through a 25 μm field-limiting aperture. The transmitted light was collected through the 50× objective and focused on the 50 μm confocal pinhole. The absorption was calculated from the transmitted light intensities for the protein solution (I) and the buffer solution ($I_0$). For comparison, the optical absorption of the solution was measured at various concentrations in a 1 cm cuvette using a conventional UV-VIS spectrometer (Cary 500i), as illustrated in FIG. 3a. The stock solution was diluted successively by adding deionized water to obtain samples with final concentrations between 0.9 mM to 6.5 mM for the micro-capillary and 4 μM to 30 μM for the standard cuvette. Data acquisition times for spectra were two seconds for the micro-capillary in the micro-absorption setup and 60 seconds for the cuvette on a scanning spectrometer. The absorbance A depends linearly on the concentration c according to $A=\epsilon Lc$, where $\epsilon$ and L denote molar extinction coefficient and pathlength, respectively. The absorption measured in a micro-capillary matched the one obtained in a 1 cm cuvette with a standard UV-Vis spectrometer. FIG. 3 combines the data from the two measurements. The results are plotted in the form A/L vs. concentration on a double-logarithmic scale, as shown in FIG. 3b. Thus the slope corresponds to the extinction coefficient $\epsilon$ for which a value of 54.9 $mM^{-1}cm^{-1}$ is obtained. This is in quantitative agreement with the literature value of 55.1 $mM^{-1}cm^{-1}$, demonstrating the linearity of the embodied technique. The data in FIG. 3 show that absorption spectra of solutions can be obtained in a micro-capillary and suggest various applications in diagnostics and microfluidics.

Figure 4:
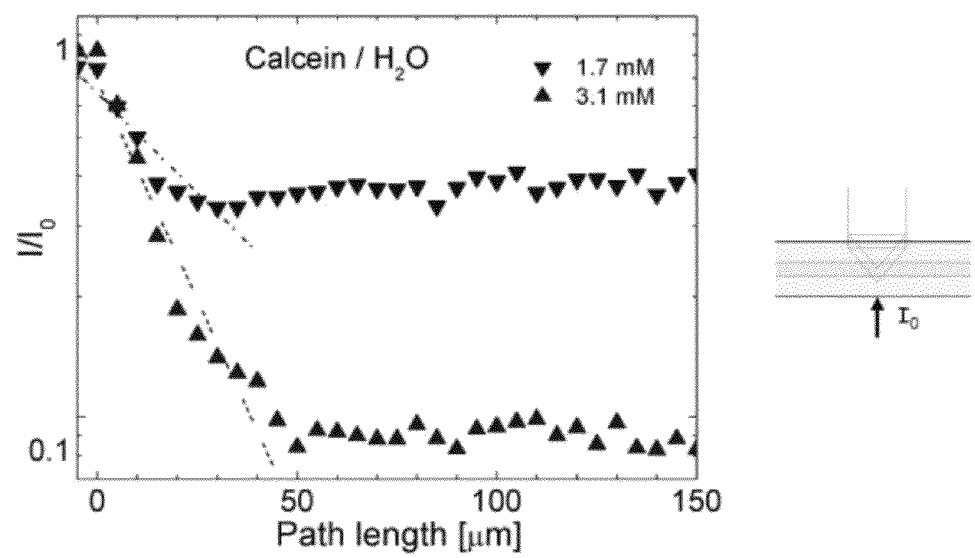
FIG. 4: Dependence of the transmitted intensity ratio $I/I_0$ on the optical pathlength in a microcapillary, according to an illustrative aspect of the invention. Note the logarithmic scale on the vertical axis. The dashed lines indicate least squares fits to Beer-Lambert law. The right panel shows a schematic of the axial sampling.

Within the micro-capillary the intensity should decrease due to absorption by dI over a distance dz according to the Beer-Lambert law: $dI=-\alpha Idz$. This provides a further test for spatial resolution. The micro-capillary with 3.1 mM calcein solution was placed in the sample holder groove and illuminated in transmission geometry. The capillary was scanned along the axial direction and the light intensity profile was measured in 5 μm steps starting from below the sample position. This was done for the buffer ($I_0$) and the dye solution (I). The intensity ratio $I/I_0$ is plotted on a semi-logarithmic scale in FIG. 4. The transmittance decreases with increasing pathlength inside the sample and then stays constant as predicted by the Beer-Lambert law. The slope of the linear part of the $I/I_0$ curve is $-0.016$ $\mu m^{-1}$. It corresponds to $\epsilon c$ and is in good agreement with the value of $-0.017$ $\mu m^{-1}$ calculated from the concentration c=3.1 mM and the molar extinction coefficient $\epsilon=55.1$ $mM^{-1}cm^{-1}$. Similarly, for a lower concentration of 1.7 mM, the slope from the measured $I/I_0$ vs. pathlength was determined as $-0.011$ $\mu m^{-1}$. Again, this is in good agreement with the value of $-0.009$ $\mu m^{-1}$ calculated from c and $\epsilon$. The linear relationship between log ($I/I_0$) and pathlength inside the sample demonstrates a spatially resolved attenuation according to the Beer-Lambert law.

Exemplary Application

Micro-Spectroscopy of Single Erythrocytes Infected with the Malaria Parasite

Red blood cells are relatively simple biological structures as they are non-nucleated and lack intra-membrane organelles. They are biconcave shaped disks, which optimize the flow properties in the vessels. They are the principle means of delivering oxygen to the organs and mainly consist of hemoglobin, a globular protein. The malaria parasite *Plasmodium falciparum* introduces mechanical changes in the host red blood cell [1,2], making it difficult for the cells to pass through the vessels. This affects the oxygen transporting capability.

Malaria is responsible for over a million deaths every year; mostly infants, pregnant women, and young children in areas endemic for the parasites [3]. Close to half of the world's population still lives in areas with high risk of contracting malaria. According to a 2009 World Health Organization report, a child dies of malaria every 30 seconds. According to the U.S. Center for Disease Control and Prevention, more than 1,400 new cases are reported annually in the United States in travelers returning from malaria-endemic areas.

The human malaria parasite has a complex life cycle that requires both a vector body (female anopheles mosquito) and a host body. The sexual reproduction of the parasite occurs in the mosquito body and the resulting sporozites are inoculated into the human host when bitten by the infection carrying mosquito. These sporozites infect the liver cells and mature themselves into schizonts, each containing thousands of merozites, which are released into the blood stream through rupturing. These merozites invade erythrocytes and go through another round of asexual reproduction in the erythrocytic cycle.

During the intra-erythrocytic stage of the life cycle the malaria parasite degrades the hemoglobin. Hemoglobin degradation by the parasite during the intra-erythrocytic cycle has been studied through experimental techniques and mathematical models and simulations. Studies suggest that hydrolysis of globin provides the principal source of amino acids for erythrocytic development and also provide sufficient space for the parasite growth [4]. Hemoglobin degradation is also essential to maintain osmotic stability of the intra-erythrocytic parasite [5]. Breaking down of hemoglobin is a complex process which involves transport of hemoglobin from cytosol to the parasite food vacuole, disruption of hemoglobin tetramers, removal of heme, detoxification of heme by the formation of hemozoin and the hydrolysis of globin by a number of proteases into amino acids.

We investigated hemoglobin degradation due to the parasite growth in the erythrocytes employing noninvasive optical techniques utilizing aspects of the embodied invention described hereinabove. Electronic absorption spectra of healthy erythrocytes and cells infected with the parasite are presented, which can be correlated to the parasite multiplication cycle. Micro-Raman spectroscopy was further employed to investigate changes in the vibrational band with hemozoin formation.

Parasites were maintained in human A+ erythrocytes at 5% hematocrit in complete RPMI-1640 (Invitrogen) supplemented with 0.5% Albumax (Gibco). Cultures were split every other day to maintain a parasitemia of 2-5%, as monitored by Geimsa stained smears, and freshly washed RBCs were added. A+ whole blood was obtained from Florida Blood Centers on a monthly basis. Whole blood was washed in incomplete RPMI to remove unnecessary components and RBCs were resuspended in complete RPMI-1640 to 50% (2% Dextrose, 15 mg/L Hypoxanthine, 0.2% Sodium Bicarbonate, 25 mM HEPES, 25 µg/ml gentamycin). Parasites were synchronized on a MACs LD Separation Columns (Miltenyi Biotec) in late trophozoite stage. Columns were placed on a magnetic stand and equilibrated with 5 ml of complete media. Parasite cultures were pelleted and resuspended in 5 ml fresh media and applied to the column. Flow through containing uninfected RBCs, ring and early trophozoite stage parasites was discarded; late trophozoites remained bound to the column. The column was then washed with 5 ml of complete media. The column was removed from the magnetic stand and parasites were eluted with 5 ml complete media. Freshly washed erythrocytes were added to the synchronized culture to obtain 4% hematocrit. The following day Geimsa stained smears of the culture were prepared to evaluate parasitemia.

Figure 5:
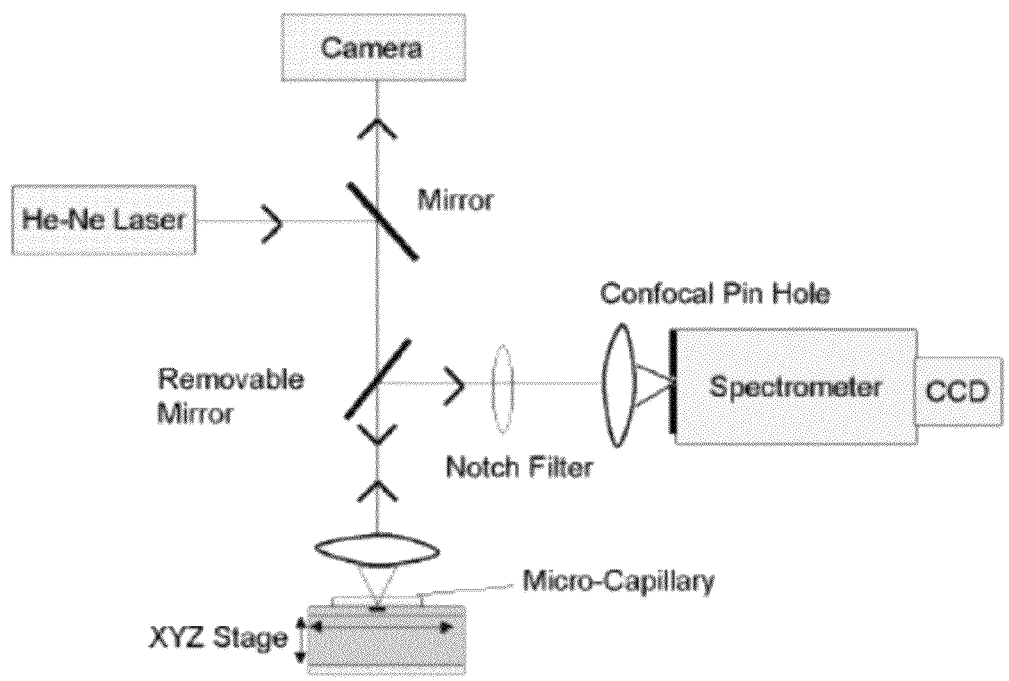
FIG. 5: Schematic of a micro-spectroscopy setup according to an illustrative, exemplary aspect of the invention. Raman scattering is excited by a He—Ne laser and the signal is collected in a back-scattering geometry. Micro-absorption spectra are measured in transmission geometry.

As illustrated in FIG. 5, Raman spectra of individual healthy and parasite infected erythrocytes were recorded on a LabRam HR 800 setup using 632.8 nm excitation from a helium neon laser (4 mW). The Raman system is coupled with an Olympus BX41 microscope with a 100× dry objective (NA=0.9). The vertically polarized laser was directed internally using a set of mirrors and focused through a lens onto the sample. The Raman signal was collected by the microscope objective in back scattering configuration through the same optical path and through a holographic notch filter to the 100 µm confocal pin hole of the spectrometer. Spectra were recorded between 1800 and 650 cm$^{-1}$ with a resolution of 1.5 cm$^{-1}$. A fused silica micro capillary with an inner bore of 50 µm and outer diameter 350 µm was used and positioned using a nanoliter sample holder. An optical window was created by burning the outer coating and wiping the capillary through ethanol. The sample was loaded in a micro-capillary by dipping one end in the sample culture, allowing capillary action to draw the cells up. The small volumes and small optical window allowed us to investigate individual cells without interference from the neighboring cells.

We employed the technique of confocal absorption microscopy as described hereinabove to measure the optical absorption spectrum with spatial resolution at the micron scale [6] to investigate the changes in the electronic absorption bands of host red blood cells after parasite infection. Our technique enabled the measurement of the absorption spectrum of a single erythrocyte between 350 and 700 nm with a lateral resolution better than 1.5 µm.

Micro-absorption spectra were measured on red blood cells immobilized on a coverslip using standard procedures. The coverslip was rinsed with 70% ethanol followed by 1× Phosphate Buffer Saline (pH 7.4). Sufficient 1 mg/ml poly-L-Lysine HBr was applied to coat the coverslips, which were then kept at room temperature for 15 minutes. Coating solution was removed and the coverslips were rinsed with 1×PBS. The erythrocytes suspended in 1×PBS were added to the coverslips and were allowed to adhere at room temperature for 20 minutes. Excess liquid was drained from the coverslip. The transmittance of an individual red blood cell was measured with a spectral resolution of 0.5 nm. Micro-absorption spectra were recorded of erythrocytes immobilized both on coverslips and in micro-capillaries and found to be in agreement.

Figure 6:
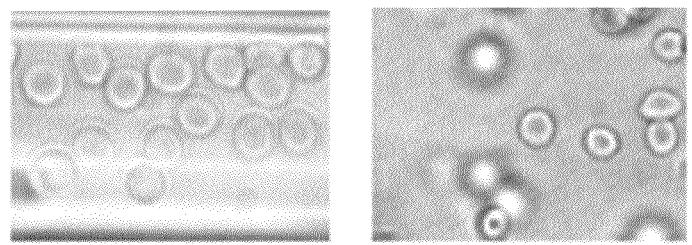
FIG. 6: Erythrocytes in a micro capillary: a) healthy; b) infected, according to an illustrative aspect of the invention. The diameter of a single cell is ~7 µm.
Figure 7:
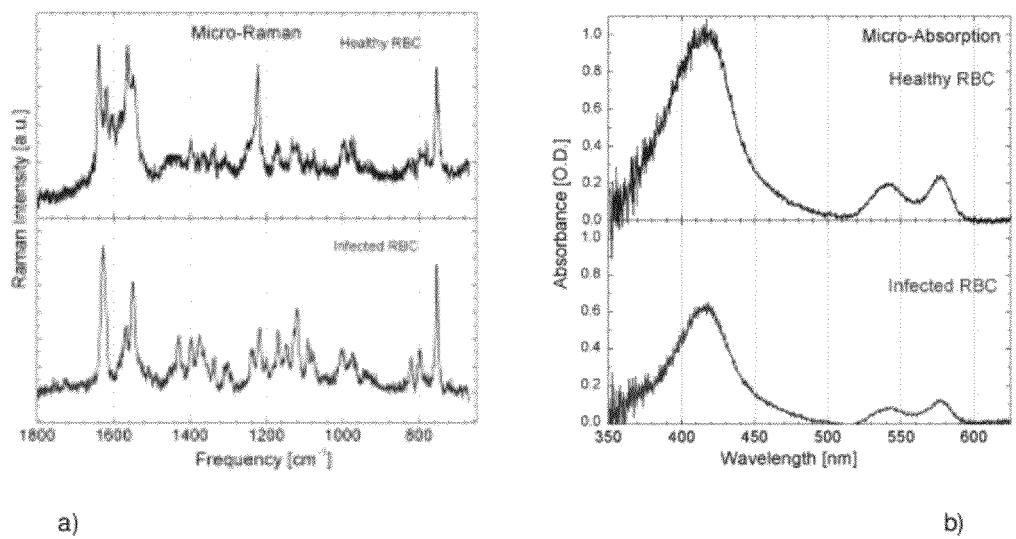
FIG. 7: a) Micro-Raman and b) micro-absorption spectra of single erythrocytes. The top spectrum in each figure is from a healthy erythrocyte. The spectra at the bottom are from erythrocytes infected with malaria parasite *Plasmodium falciparum*, according to an illustrative aspect of the invention.

Optical microscopy images of healthy human RBCs and RBCs infected with malaria inducing parasite *Plasmodium falciparum* are shown in FIGS. 7a, b, respectively. The cells are contained in a micro-capillary of inner bore 50 µm. The image in FIG. 6b shows the cell with the parasite in it at 24 hr post invasion. Through optical images without stains it is difficult to discern between healthy and infected cells and to correlate them to parasite multiplication cycle. The results that follow show the micro-absorption as a potential diagnostic marker for different stages of parasite multiplication cycle.

Micro-Raman spectra of a healthy red blood cell and a cell infected with *Plasmodium falciparum* are shown in FIG. 2a. The excitation wavelength was 633 nm. The bands in the spectra mainly arise from porphyrin vibrations [7]. The Raman scattering enhancement observed at 632.8 nm may result from excitonic coupling between aligned porphyrins due to the close proximity of heme moieties [8]. The vibrational bands are indicative of hemoglobin, the major protein in the cell. They can be grouped into the following regions: 1500-1650 cm$^{-1}$: core size or spin state marker band region. 1450-1300 cm$^{-1}$: pyrole breathing mode region, ν4. 1300-1200 cm$^{-1}$: methine C—H deformation region. 1450-1300 cm$^{-1}$: pyrole ring breathing mode, ν15. The peak positions are dependent on oxidation state. While a band at 1545 cm$^{-1}$ is the most intense peak in deoxygenated cells, the spectra show clearly two different peaks at 1548 cm$^{-1}$ and 1565 cm$^{-1}$. The ν13 mode of the oxygenated heme has a frequency of 1224 cm$^{-1}$ compared to 1211 cm$^{-1}$ in the deoxy state. These peaks are representative of those seen in oxygenated cells as these bands are dependent on oxidation state and on whether the heme has bound oxygen [8]. The 1500-1650 cm$^{-1}$ region is dominated by the core size (or spin state marker band). There are clear differences between *Plasmodium falciparum* infected and uninfected cells in this region, and in the broadening of the peaks near 1210-1230 cm$^{-1}$ (C—H methine deformation band) and 755 cm$^{-1}$ (pyrrole ring breathing mode). The spectral changes are in agreement with those reported by Wood and co-workers in independent experiments [9]. As the hemoglobin is broken down by the parasite, the protein chain fragments are transported away for further digestion. The remaining toxic heme is then oxidized to a ferric state. The release of the heme from the protein is the first step in the formation of hemozoin. The changes in the spectra could be the result of this degradation and the changes in the vibrational modes of the now free heme. As the heme rings are no longer bound within the pocket of the protein the constraints on the various bonds will be much more random which accounts for the broadening of the bands.

FIG. 2b shows the micro-absorption spectrum of individual erythrocyte in the healthy and infected state. An individual live erythrocyte under physiological condition was illuminated using broadband excitation and the transmitted light intensity was collected using the spectrometer with five seconds acquisition time. The spectrum was obtained over the visible range from 350 to 700 nm. The electronic absorption spectra of porphyrins feature two weak visible transitions near 555 nm and the intense Soret transition near 400 nm [10]. The intense absorption bands result from to $\pi$ to $\pi^*$ transitions and can be distinguished from the weak bands due to charge transfer transitions. The spectra depend on the electronic configuration of the iron cation and can be correlated to the spin state [10]. The absorption spectrum of the healthy red blood cell is indicative of oxygenated hemoglobin with the Soret band at 415 nm and $\beta$- and $\alpha$-bands at 541 and 577 nm, respectively. The ratio of relative intensities of $\beta$- and $\alpha$-bands was calculated to be 0.87 as compared to the literature value of 0.92 [11].

Changes in peak positions and relative peak intensities were observed in the case of cells in pathological conditions. The Soret band was weaker than in uninfected sample and was shifted to 418 nm. The $\beta$- and $\alpha$-bands moved to 543 and 576 nm, respectively. The ratio of the relative intensities of the two bands decreased to 0.67. The peaks were broader and less intense in the infected sample.

Understanding the structural changes in the degradation of hemoglobin may opens new targets for anti-malarial drug treatments. Observing the cells in a native-like environment facilitates the transfer of new diagnostics for faster detection of the parasite's presence in the human body.

REFERENCES

[1] Y. K. Park, M. Diez-Silva, G. Popescu, G. Lykotrafitis, W. Choi, M. S. Feld, and S. Suresh, "Refractive index maps and membrane dynamics of human red blood cells parasitized by *Plasmodium falciparum*," *Proceedings of the National Academy of Sciences*, vol. 105, pp. 13730, 2008.

[2] S. Suresh, "Mechanical response of human red blood cells in health and disease: some structure-property-function relationships," *J. Mater. Res*, vol. 21, pp. 1871, 2006.

[3] "US Department of Health and Human Services National Institutes of Health National Institute of Allergy and Infectious Diseases NIH Publication No. 02-139," 2002.

[4] I. W. Sherman, *Molecular approaches to malaria*: Amer Society for Microbiology, 2005.

[5] V. L. Lew, T. Tiffert, and H. Ginsburg, "Excess hemoglobin digestion and the osmotic stability of *Plasmodium falciparum*-infected red blood cells," *Blood*, vol. 101, pp. 4189, 2003.

[6] S. Arora, J. Mauser, D. Chakrabarti, and A. Schulte, "Spatially resolved micro-absorption spectroscopy with broadband source and confocal detection," to be submitted.

[7] B. R. Wood, B. Tait, and D. McNaughton, "Micro-Raman characterisation of the R to T state transition of haemoglobin within a single living erythrocyte," *Biochimica et Biophysica Acta (BBA)-Molecular Cell Research*, vol. 1539, pp. 58, 2001.

[8] B. Wood, D. McNaughton, "Raman excitation wavelength investigation of single red blood cells in vivo," *J. Raman Spectrosc.*, vol. 33, pp. 517, 2002.

[9] B. R. Wood, S. J. Langford, B. M. Cooke, J. Lim, F. K. Glenister, M. Duriska, J. K. Unthank and D. McNaughton, "Resonance Raman Spectroscopy Reveals New Insight into the Electronic Structure of $\beta$-Hematin and Malaria Pigment," *J. Am. Chem. Soc.*, vol. 126, pp. 9233, 2004.

[10] M. W. Makinen, A. K. Churg, A. B. P. Lever, and M. B. Gray, "Iron Porphyrins Part 1," Addison-Wesley Publishing Co., Massachusetts, 1983.

[11] E. Antonini and M. Brunori, *Hemoglobin and Myoglobin in their Reactions with Ligands*: North-Holland Pub. Co., 1971.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening.

The recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not impose a limitation on the scope of the invention unless otherwise claimed.

No language in the specification should be construed as indicating any non-claimed element as essential to the practice of the invention.

It will be apparent to those skilled in the art that various modifications and variations can be made to the present invention without departing from the spirit and scope of the invention. There is no intention to limit the invention to the specific form or forms disclosed, but on the contrary, the intention is to cover all modifications, alternative constructions, and equivalents falling within the spirit and scope of the invention, as defined in the appended claims. Thus, it is intended that the present invention cover the modifications and variations of this invention provided they come within the scope of the appended claims and their equivalents.

We claim:

1. A transmission-geometry, optical absorbance spectroscopy apparatus, comprising:
   a broadband sample illumination source providing broadband sample illumination;
   a broadband sample illumination propagation medium that is an optical waveguide having a proximal end and a distal end;
   a sample holder;
   a sample field-of-view controller comprising a sample field-of-view aperture having a maximum dimension less than 50 micrometers ($\mu$m) disposed at the distal end of the optical waveguide, which is coupled to the sample holder, wherein the proximal end is coupled to the broadband sample illumination source, wherein the sample field-of-view aperture provides a limiting sample field of view of the broadband sample illumination; and
   a transmitted light detection path comprising a portion of the broadband sample illumination that is transmitted by the sample.

2. The apparatus of claim 1, wherein the broadband sample illumination source is a broadband white light source.

3. The apparatus of claim 1, wherein the sample field-of-view is a clear aperture diameter between 5 to 35 μm.

4. The apparatus of claim 1, wherein the sample field-of-view aperture is a clear aperture diameter between 5 to 25 μm.

5. The apparatus of claim 1, wherein the broadband sample illumination source comprises at least two illumination sources having different illumination spectra.

6. The apparatus of claim 1, wherein the sample holder is adapted to hold at least one of a microcapillary and a microfluidic device having a microchannel.

7. The apparatus of claim 1, further wherein the distal end of the optical waveguide is disposed in an alignment fixture that is seated in a given location of the sample holder.

8. The apparatus of claim 1, wherein the transmitted light detection path comprises an optical microscope adapted to collect the broadband sample illumination transmitted by the sample; and
a detector adapted to receive an output of the optical microscope.

9. The apparatus of claim 5, wherein the at least two illumination sources include at least two light emitting diodes (LEDs).

10. The apparatus of claim 6, wherein the sample holder further comprises an x-y-z translation stage on which the sample holder is mounted.

11. The apparatus of claim 7, further comprising an x-y-z translation stage on which the sample holder is mounted.

12. The apparatus of claim 8, wherein the detector further comprises a spectrometer.

13. The apparatus of claim 8, wherein the broadband sample illumination source is a broadband white light source.

14. The apparatus of claim 8, wherein the broadband sample illumination source comprises at least two illumination sources having different illumination spectra.

15. The apparatus of claim 8, wherein the sample holder is adapted to hold at least one of a microcapillary and a microfluidic device having a microchannel.

16. The apparatus of claim 8, wherein the optical microscope is a confocal system.

17. The apparatus of claim 14, wherein the at least two illumination sources include at least two light emitting diodes (LEDs).

18. The apparatus of claim 15, wherein the sample holder further comprises an x-y-z translation stage on which the sample holder is mounted.

19. The apparatus of claim 16, wherein the confocal system is a free-space confocal system.

20. The apparatus of claim 16, further comprises a confocal aperture having a diameter between 10 to 50 microns.

21. A method for performing transmission-based optical absorption spectroscopy of a sample, comprising:
illuminating a sample with a broadband illumination spectrum from a broadband sample illumination source;
limiting a sample illumination field of view having a maximum dimension less than 50 μm;
transmitting the broadband illumination spectrum to the sample via an optical waveguide having a proximal end coupled to the broadband sample illumination source and a distal end, wherein a sample field-of-view aperture is disposed at the distal end of the optical waveguide, which is coupled to a sample holder;
aperturing the illumination at the distal end of the optical waveguide to limit the sample illumination field of view; and
detecting a transmitted portion of the broadband illumination spectrum.

22. The method of claim 21, further comprising limiting the sample illumination field of view having a maximum dimension between 5 to 35 μm.

23. The method of claim 21, further comprising illuminating the sample with a broadband white light illumination spectrum.

24. The method of claim 21, further comprising:
confocally imaging the broadband illumination spectrum light that is transmitted by the sample;
inputting the confocally imaged light into a spectrometer; and
obtaining the optical absorption spectrum of the sample.

25. The method of claim 24, further comprising scanning the sample with the illuminating light in an axial direction.

26. The method of claim 24, further comprising providing the sample in a micro-capillary.

27. The method of claim 24, further comprising providing the sample in a microchannel of a microfluidic device.

28. The method of claim 24, wherein the step of confocally imaging the illumination light that is transmitted by the sample further comprises providing a confocal aperture having a diameter between 10 to 50 microns.

29. The method of claim 24, wherein the sample comprises a red blood cell.

30. The method of claim 28, wherein the step of obtaining the optical absorption spectrum further comprises adjusting the diameter of the confocal aperture.

31. The method of claim 29, wherein the sample further comprises a red blood cell infected with *Plasmodium falciparum*.

* * * * *